(12) United States Patent
Peters

(10) Patent No.: US 11,083,403 B1
(45) Date of Patent: Aug. 10, 2021

(54) PULMONARY HEALTH ASSESSMENT SYSTEM

(71) Applicant: Cortery AB, Domsten (SE)

(72) Inventor: Filip Ludwig Peters, Domsten (SE)

(73) Assignee: Cortery AB, Domsten (SE)

(*) Notice: Subject to any disclaimer, the term of this patent is extended or adjusted under 35 U.S.C. 154(b) by 0 days.

(21) Appl. No.: 16/949,044

(22) Filed: Oct. 11, 2020

(51) Int. Cl.
| | |
|---|---|
| *A61B 5/01* | (2006.01) |
| *A61B 5/332* | (2021.01) |
| *A61B 5/00* | (2006.01) |
| *A61B 5/026* | (2006.01) |
| *A61B 5/024* | (2006.01) |
| *A61B 5/25* | (2021.01) |
| *A61B 5/339* | (2021.01) |

(52) U.S. Cl.
CPC ............ *A61B 5/332* (2021.01); *A61B 5/01* (2013.01); *A61B 5/0261* (2013.01); *A61B 5/02416* (2013.01); *A61B 5/25* (2021.01); *A61B 5/339* (2021.01); *A61B 5/7264* (2013.01); *A61B 5/7275* (2013.01); *A61B 2562/0219* (2013.01); *A61B 2562/166* (2013.01)

(58) Field of Classification Search
CPC . A61B 5/0404; A61B 5/0261; A61B 5/07264; A61B 5/01; A61B 5/7275; A61B 5/05416; A61B 5/0408; A61B 5/044; A61B 2562/0219; A61B 2562/166
See application file for complete search history.

(56) References Cited

U.S. PATENT DOCUMENTS

| | | | |
|---|---|---|---|
| 2015/0018660 A1* | 1/2015 | Thomson | A61B 5/0404 600/393 |
| 2015/0263777 A1* | 9/2015 | Fraden | A61B 5/6898 455/575.8 |
| 2018/0144092 A1* | 5/2018 | Flitsch | C12Q 1/6886 |
| 2019/0110692 A1* | 4/2019 | Pardey | A61B 5/7282 |
| 2020/0077917 A1* | 3/2020 | Sayani | A61B 5/0006 |
| 2020/0225811 A1* | 7/2020 | Sieniek | G06F 3/04883 |
| 2020/0288985 A1* | 9/2020 | Robinson | A61B 5/0205 |

* cited by examiner

*Primary Examiner* — Rex R Holmes
(74) *Attorney, Agent, or Firm* — Michael P. Eddy

(57) ABSTRACT

A pulmonary health assessment system for use with a handheld electronic device (HED) that includes a casing having a shape adapted to secure the HED with the casing. The casing includes a plurality of electrodes and a circuit board. The electrodes capture data indicative of the pulmonary health of the user. The circuit board includes a microphonic sensor, a diaphragm, a Photoplethysmography (PPG) sensor, an Inertial Measurement Unit (IMU) sensor, and a microcontroller. The microphonic sensor captures pulmonary audio signals indicative of the pulmonary health of the user. The diaphragm enhances the pulmonary audio signals. The PPG sensor measures pulmonary capillary blood flow. The IMU sensor captures seismic and auscultation signals indicative of the pulmonary health of the user. The microcontroller transmits pulmonary health data to the handheld electronic device and a computing device.

22 Claims, 12 Drawing Sheets

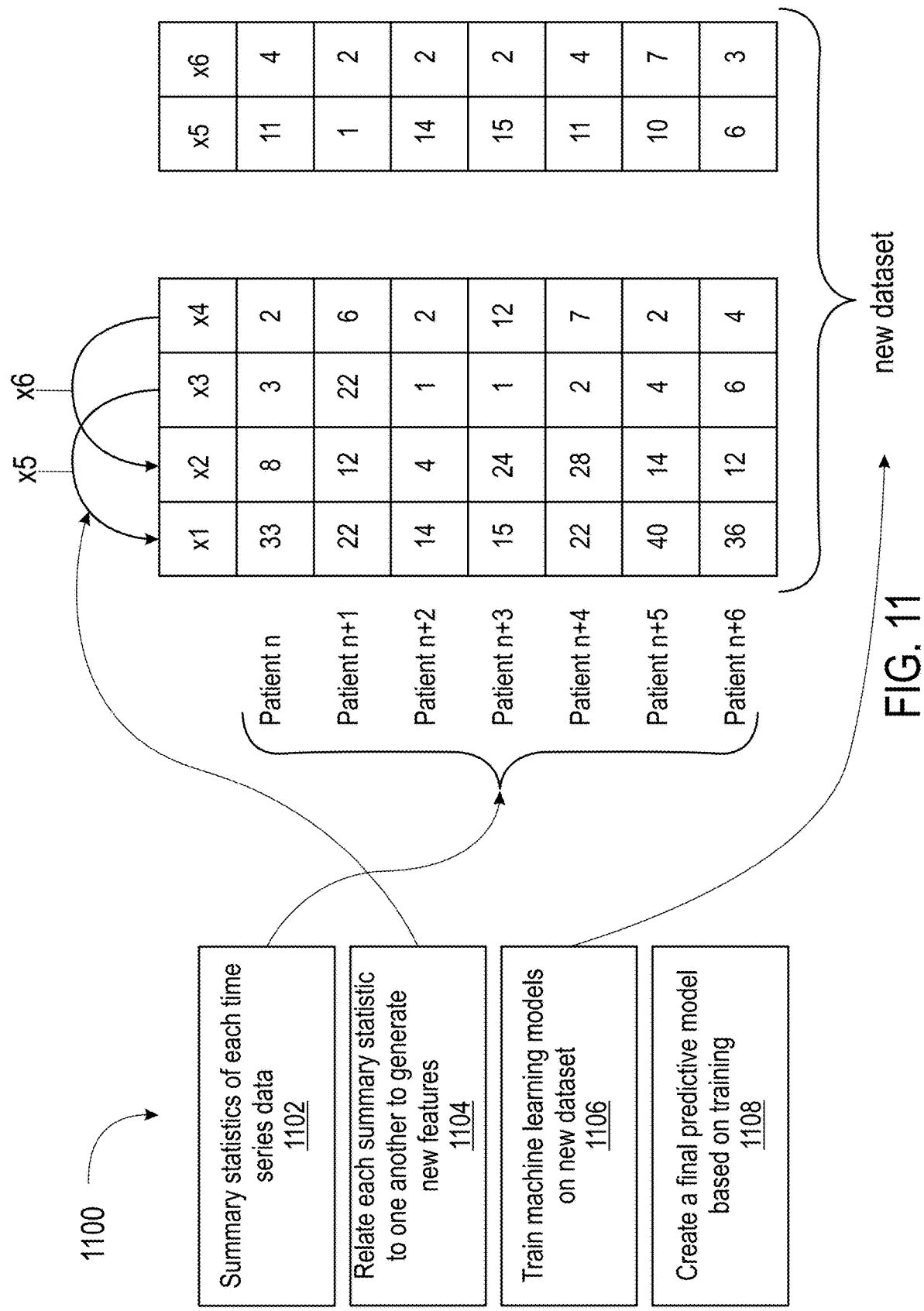

PULMONARY HEALTH ASSESSMENT SYSTEM

BACKGROUND

Technical Field

The inventive subject matter presented herein is generally directed towards pulmonary health assessment systems and methods for use with a handheld electronic device (HED). More particularly embodiments are related to, but not limited to, pulmonary health assessment systems for analyzing and detecting an unhealthy lung due to lung cancer, pulmonary embolism and/or pulmonary fibrosis.

Description of the Related Art

Artificial intelligence (AI) and machine learning (ML) enabled medicine and healthcare products are used to effectively support patients with long term conditions at home. In particular, AI can be useful in the absence of conclusive evidence of decision-making AI can help to analyze continuous data received from patients infected and not infected with a lung disease in real-time to understand and predict if the lung disease is present or evolving in the patient's body. In a pandemic situation, the available number of healthcare professionals are reduced to treat those patients affected by lung diseases. AI can help to identify those patients who need attention and channel them to healthcare professionals so they can focus on delivering healthcare.

Currently, pulmonary (relating to the lungs) diseases or disorders are common all over the world. The pulmonary diseases are classified into various categories such as breathing rhythm disorders, obstructive diseases, restrictive diseases, infectious diseases, pulmonary vasculature disorders, pleural cavity disorders, and the like. Among the most widespread pathologies of the respiratory system can be identified as a chronic obstructive pulmonary disease (COPD), tuberculosis, respiratory infections of the lower respiratory tract, oncology, as well as many others. Pulmonary diseases can be associated with a decrease in the total volume of exhaled airflow caused by a narrowing or blockage of the airways. Examples of COPD include asthma, emphysema, and bronchitis.

Further, pulmonary diseases may be caused by infectious agents such as viral and/or bacterial agents. Examples of infectious pulmonary diseases include pneumonia, tuberculosis, and bronchiectasis. Non-infectious pulmonary diseases include lung cancer and adult respiratory distress syndrome (ARDS), for example. In cases where pulmonary diseases can be detected and diagnosed at an early stage, the likelihood of successful treatment can be improved.

Many pulmonary conditions are analyzed by radiologists to determine and diagnose the likely causes of physical symptoms. Chest X-rays and/or Computed Tomography (CT) scans may be used by clinicians to gain a better understanding of what conditions may be present and to what extent. These methods can have problematic issues. Some disadvantages of Chest X-rays and CT-scans is that patients may be exposed to radiation and in patients with significant kidney problems, the use of contrast material (dye) can be harmful. They can also be expensive to use. These methods can also be unsuitable for continuous and regular monitoring of patients' health conditions as well as for broad-scale screening purposes across a population for use in identifying and treating conditions early.

Therefore, there is a need for a pulmonary health assessment systems and methods that can provide a better patient experience by enabling the patients to self-monitor their lung conditions. There is also a need for an affordable and accurate screening tool that can help rule-in patients who may benefit from early identification and treatments of certain conditions. For example, the survival rates of lung cancer patients have been shown to improve with early identification of the presence of this disease. Thus, there is a need for systems, devices and methods that can accurately measure one or more different pulmonary conditions simultaneously while also providing data and processing for health assessments of such conditions. There is also a need to integrate such pulmonary health assessment systems and devices with computing devices that continue to increase in computing power and capability. Power management can also reduce the need to keep track of charging a pulmonary health assessment. Helping patients keep track of their pulmonary health assessment devices so that they do not misplace them as easily is another need.

Thus, in view of the above, there is a long-felt need in the healthcare industry to address the described issues.

SUMMARY

Pulmonary health assessment systems for use with a handheld electronic device (HED) are provided and shown in and/or described in connection with the figures.

One aspect of the inventive subject matter relates to pulmonary health assessment systems for use with a handheld electronic device (HED). In many of the embodiments, the pulmonary health assessment system includes a casing with the casing having a shape adapted to secure the handheld electronic device with the casing. The casing includes a plurality of electrodes and a circuit board. The electrodes include a first ECG electrode, a second ECG electrode, and a third electrode. The first ECG electrode is placed on an outer surface of the casing. The second ECG electrode and the third electrode are placed on each side of the casing to facilitate a thumb and fingers of a user to be placed on the casing having the shape that is adapted to secure the handheld electronic device. The casing further includes a diaphragm. The electrodes are configured to capture data indicative of the pulmonary health of the user. The circuit board is configured within the casing and electrically connected with the plurality of electrodes. The circuit board is connected to a microcontroller. A microphonic sensor, a Photoplethysmography (PPG) sensor, and an Inertial Measurement Unit (IMU) sensor is connected to a microcontroller. The microphonic sensor captures pulmonary audio signals indicative of the pulmonary health of the user. The diaphragm enhances the pulmonary audio signals captured by the microphonic sensor. The PPG sensor measures pulmonary capillary blood flow. The IMU sensor captures seismic and auscultation signals indicative of the pulmonary health of the user. The microcontroller transmits pulmonary health data received from the plurality of electrodes, the microphonic sensor, the PPG sensor, and the IMU sensor to the handheld electronic device and a computing device.

Pulmonary health may be assessed based on the presence of abnormalities and deviations from a typical patient's normal lung function. For example, abnormal masses or nodules may be observed using non-invasive sensor technologies. Small lesions in a patient's lungs may furthermore be indicative of pulmonary health conditions pertaining to cancer and/or other diseases. Physical symptoms arising from pulmonary health deterioration, e.g. if a patient has a cough and/or is producing sputum may be discovered through deviations in seismic and/or audio waveforms. Inflammation in the lungs may also be discovered using the technologies described herein through deviations from normal audio, seismic, photoplethysmographic and/or electrocardiographic readings of lung function. Scarring of the lungs can leave lasting marks on a patient's pulmonary health that may be indicative pulmonary fibrosis and may be identified by certain bilateral fine crackles such as a "Velcro-like" or similar distinctive sound. The progression of certain types of pulmonary health conditions may furthermore be assessed by analyzing the severity of the deviations from a normal lung.

In an embodiment, the computing device is configured to receive, in one or more temporal windows, a representation of one or more of the IMU sensor, the plurality of electrodes, the PPG sensor, and the microphonic sensor signal recorded by the casing. The computing device is configured to use data to receive features of the IMU sensor, the PPG sensor, and the microphonic sensor from at least one or more portions of the received representations falling within each of the one or more temporal windows. The computing device is configured to use sensor data to identify patterns of the features of respective sensors from within the one or more portions based on at least a classification model or a regression model. The computing device is configured to calculate, basis the identified patterns, a probability of whether one or more portions corresponds to a problem with the pulmonary health of the user.

In an embodiment, the PPG sensor generates infrared (IR) light to measure the pulmonary capillary blood flow.

In an embodiment, the HED secured with the casing comprises a display screen to display pulmonary diagnostic information derived from the pulmonary health data received from the microcontroller. In many embodiments, the HED can be secured with the casing as well as within the casing and secured with the casing encompasses secured within the casing.

In another embodiment, the casing is configured to capture pulmonary health data of the user when the casing is positioned against the chest of the user.

In another embodiment, the casing is configured to capture pulmonary health data of the user when the casing is positioned against the back of the user.

In another embodiment, when the casing is configured to capture pulmonary health data of the user when positioned against the back of the user, the collection of data from electrodes is deactivated.

In another embodiment, the casing is configured to capture pulmonary health data of the user when positioned against the thoracic cavity of a user.

In yet another embodiment, the HED secured with the casing comprises a processor to execute a plurality of instructions pertaining to a pulmonary monitoring application. The processor is configured to display one or more commands to position the casing against the chest of the user. The processor further instructs the user (patient) to hold the casing against his/her chest using one hand.

In another embodiment, the classification model is trained to detect an unhealthy lung due to severe acute respiratory syndrome (SARS).

In another embodiment, the classification model is trained based on data received from one or more of computerized tomography (CT) scans of the lung, X-ray of the chest, spirometer data, magnetic resonance imaging (MRI) data, and ultrasound data.

In another embodiment, the casing further comprises a heat-sensing camera to detect variations in chest skin surface temperature resulting from variations in the pulmonary capillary blood flow. In other embodiments, the heat-sensing camera may be external to the casing.

In another embodiment, the diaphragm includes an enhancer unit such as a bell-like object to amplify low-frequency auscultation signals pertaining to the pulmonary audio signals.

In another embodiment, the casing further comprises a battery configured to supply electrical power to the circuit board. In other embodiments, the battery may be held externally to the casing.

In other embodiments, the casing further comprises a lens configured to envelop a camera of the handheld electronic device. The lens may also be configured to envelop a portion of the camera. In these embodiments, the lens is configured to block external light when the HED shines a light onto the skin of the user. In some embodiments, video in additional to or instead of one or more images may be recorded by the camera. The camera is used to record one or more images of the user's skin and the one or more images are analysed by the system using machine learning to aid in providing insights into the pulmonary health of the user based on differences in the user's tissue color detected and applying machine learning, such as applying one or more image recognition machine learning models with the one or more images to aid in providing insights into lung conditions.

In yet another embodiment, the pulmonary health assessment system further includes a second HED worn by the user with the second HED wirelessly connected with the first HED. The second HED includes sensors that can be used to collect health data from the user. The second HED further includes a HED wireless transceiver configured to establish a communication with the computing device to transmit pulmonary health data to the computing device.

In another embodiment, the computing device is configured to detect, based on the classification model, the presence of indicators of a lung disease in a user, and use the data with a regression model to estimate the severity of the lung disease.

In another embodiment, the casing includes a plurality of additional seismic and microphonic sensors, to facilitate the identification of common ambient environmental noise unrelated to the patient's pulmonary health. In other embodiments one or more additional seismic or microphonic sensors may be used with the embodiments.

In another embodiment, the casing includes an ultrasound transducer to monitor ultrasonic pulmonary health signals.

In other embodiments, the casing further includes a magnet, one or more radiofrequency coils, and a gradient coil to enable identification of pulmonary activity through a pulmonary magnetic resonance function.

In other embodiments, the data indicating a high severity of a lung disease triggers a message transmission to one or more healthcare professionals. The message may be an electronic communication such as an electronic message, a SMS text message or a phone call.

In other embodiments, the user is guided by the HED as where to place the device on a user's body. In these embodiments, the HED can provide one or more instructions to the user as well as a third party. The HED can, instead or in addition, provide the user with one or more corrective instructions, for example by electronic message such as with an electronic display or with voice instruction so that the embodiment is placed correctly on a user.

In some embodiments, the pulmonary health risk assessment system uses the data collected by the embodiments to identify the unique physiological markers of the user.

In many embodiments, the classification model is trained to detect an unhealthy lung due to lung cancer. The classification model can be initially trained during the manufacturing process or it can also be trained during one or more uses of the embodiments or it can be trained using both methods. Embodiments can also be updated on a periodic basis to improve the algorithms in the model.

In some embodiments, the processor is configured to transmit the data indicative of pulmonary health from the handheld electronic device to a server over a network where the data can be stored and used for subsequent analysis by a clinician.

In many embodiments, the processor is configured to transmit the data indicative of lung function from the HED to a computing device via the internet so that the data can be analysed remotely.

In many embodiments, the microcontroller utilizes a de-noising algorithm, for example a machine learning library such as TensorFlow Lite.

In many embodiments, the casing is adjustable to fit any size of HED. For example, a typical size for an HED is one that would fit in a user's hand. Other sized may be smaller or larger than a user's hand.

In many embodiments, the pulmonary health assessment system, method or device may be physically incorporated into a handheld electronic device such as a smartphone and/or tablet. Methods may also be incorporated into other hardware components such as smartphones and other computing devices.

Accordingly, one advantage of the present inventive subject matter is that it enables a non-invasive and affordable methods of health assessment to identify conditions of the lungs aiding in treatment and preventive care for patients.

These features and advantages of the present disclosure may be appreciated by reviewing the following description of the present disclosure, along with the accompanying figures wherein like reference numerals refer to like parts.

BRIEF DESCRIPTION OF THE DRAWINGS

The accompanying drawings illustrate the embodiments of systems, methods, and other aspects of the disclosure. A person with ordinary skills in the art will appreciate that the illustrated element boundaries (e.g., boxes, groups of boxes, or other shapes) in the figures represent an example of the boundaries of such elements. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which:

FIG. 11 illustrates a flow diagram of using data for model training in accordance with embodiments of the claimed subject matter.

DETAILED DESCRIPTION

The present disclosure is best understood with reference to the detailed figures and description set forth herein. Various embodiments of the present systems, devices and methods have been discussed with reference to the figures. However, those skilled in the art will readily appreciate that the detailed description provided herein including the figures are presented for explanatory purposes and the embodiments extend beyond the currently described embodiments. For instance, the teachings and results presented in any particular described application may yield multiple alternative approaches and may be implemented in any suitable manner.

The described embodiments may be implemented manually, automatically, and/or a combination of thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the embodiments pertains. Persons skilled in the art will envision many other possible variations that are within the scope of the claimed subject matter.

Figure 1:
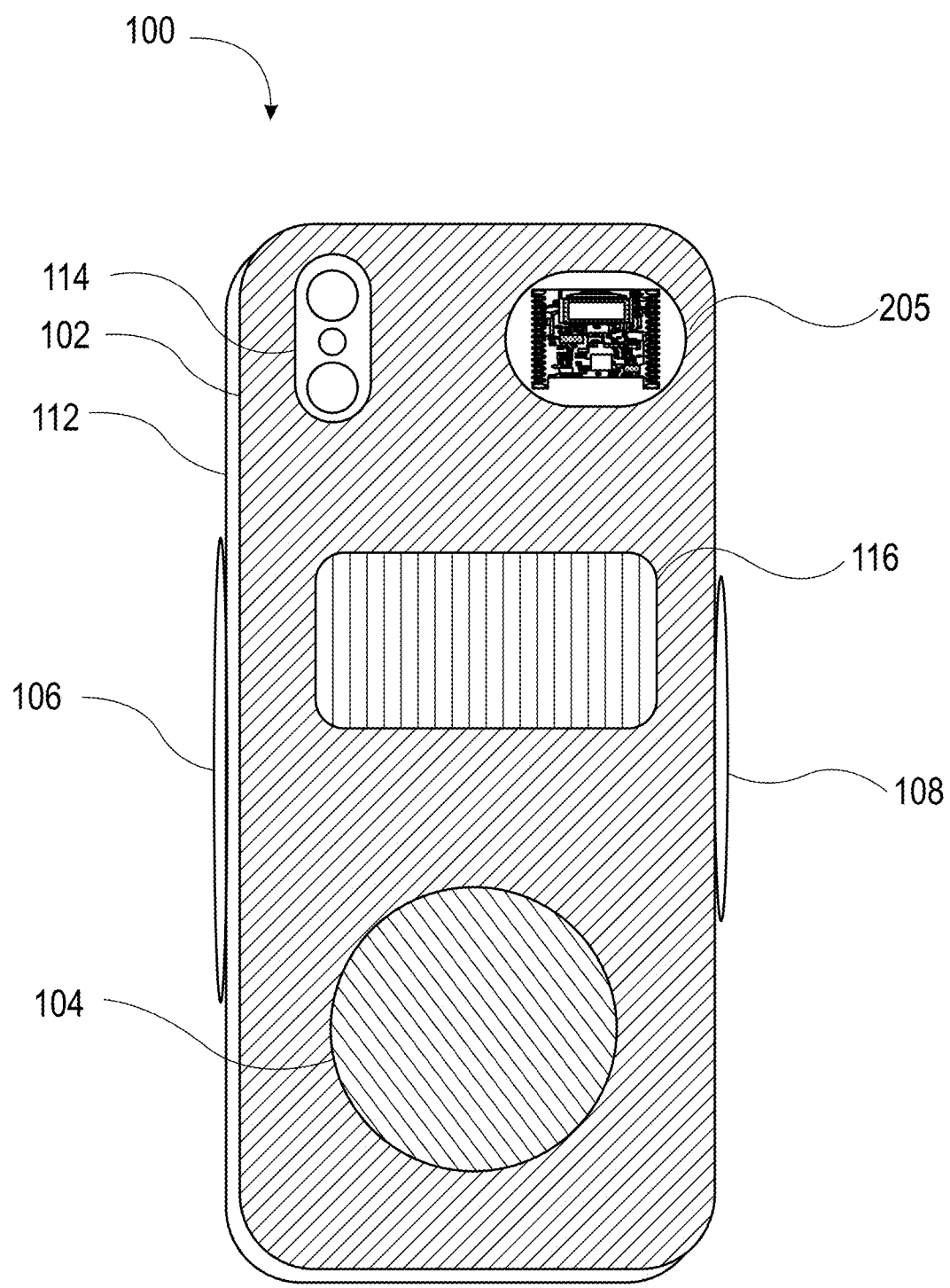
FIG. 1 illustrates a perspective view of the various components of the present pulmonary health assessment system for use with a handheld electronic device (HED) in accordance with at least one embodiment of the claimed subject matter.
Figure 2:
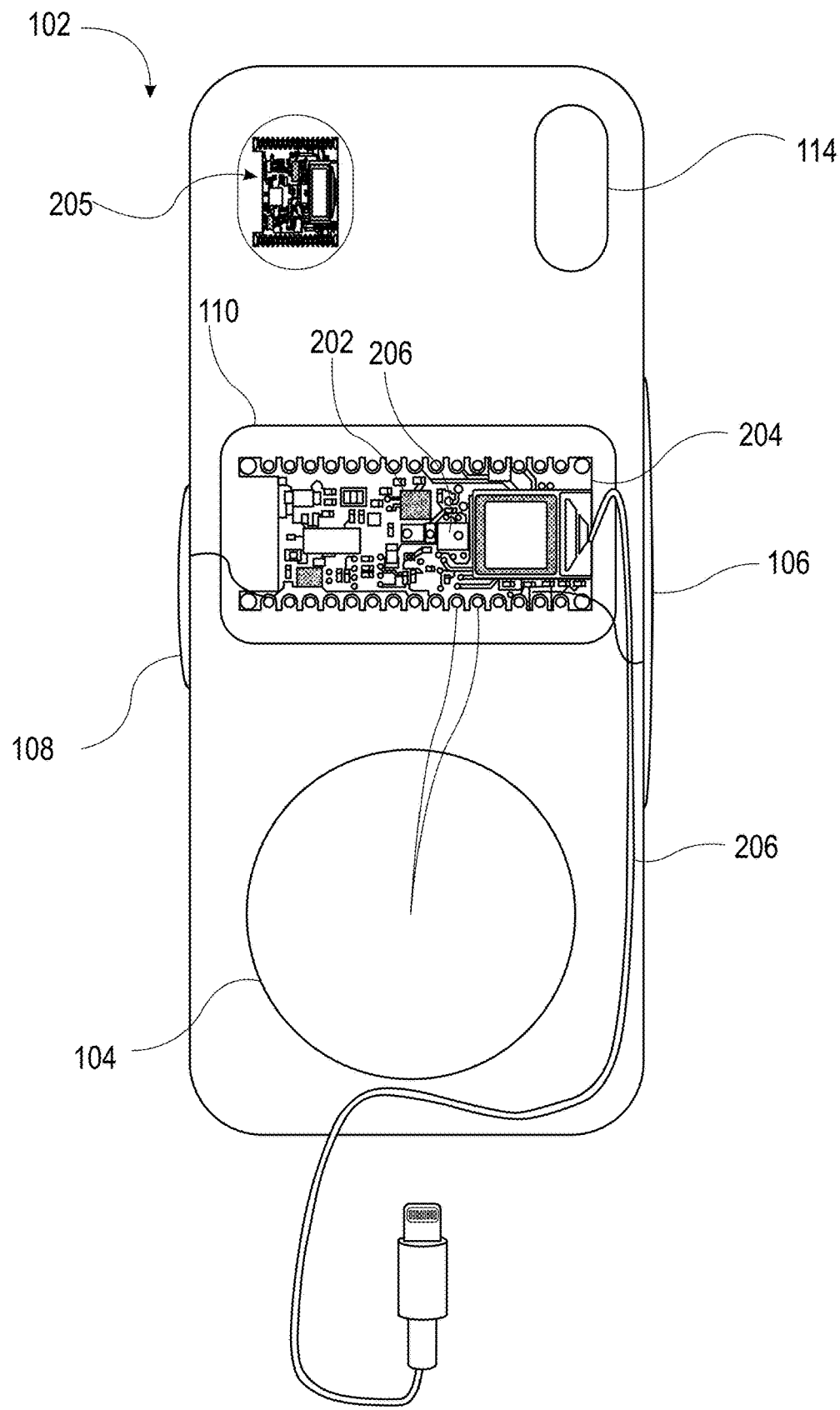
FIG. 2 illustrates an exploded view of the various components of the casing in accordance with embodiments of the claimed subject matter.

FIG. 1 illustrates a perspective view of an embodiment 100 which includes various components for use with a handheld electronic device (HED) 112. Embodiment 100 includes a casing 102 having a shape adapted to secure the handheld electronic device (HED) 112 that can be positioned with at least a portion of the casing 102. In many embodiments, the positioning of the HED 112 with a casing 102 may encompass or include the positioning of the HED 112 within all or a portion of the casing 102. In many embodiments, the shape of the casing 102 can be adapted for any suitable HED 112, for example a mobile phone or smartphone. In these embodiments, the HED 112 can be accommodated within and positioned securely within all or a portion of the casing 102. In these embodiments, the casing 102 includes a plurality of electrodes 104, 106, and 108 and a circuit board 110. As shown in FIG. 2, plurality of electrodes include a first ECG electrode 104, a second ECG electrode 106, and a third electrode 108. The first ECG electrode 104 is placed on an outer surface of the casing 102. The second ECG electrode 106 and the third electrode 108 are placed on each side of the casing 102 to facilitate a thumb and fingers of a user to be placed on the casing 102 with the casing 102 having a shape that is adapted to secure the HED 112. In these embodiments, the electrodes 104, 106, and 108 are configured to capture data indicative of the pulmonary health of the user.

FIG. 2 illustrates an exploded view of the various components of the casing 102 in accordance with embodiments of the claimed subject matter and can be viewed in conjunction with FIG. 1. As shown in FIG. 2, the circuit board 110, configured within the casing 102, is electrically connected with the plurality of electrodes 104, 106, and 108. In these embodiments, the circuit board 110 includes a microphonic sensor 202, a diaphragm 204, a Photoplethysmography (PPG) sensor 205, an Inertial Measurement Unit (IMU) sensor 206, and a microcontroller (not shown.) The microphonic sensor 202 captures pulmonary audio signals indicative of the pulmonary health of the user. The diaphragm 204 enhances the pulmonary audio signals captured by the microphonic sensor. In many embodiments, the diaphragm 204 includes an enhancer unit such as a bell-like object to amplify low-frequency auscultation signals pertaining to the pulmonary audio signals. The bell-like object may be any suitable enhancing element known to those skilled in the art. In some embodiments, the diaphragm 204 may be configured as a tube structure to enhance low-frequency sounds although the tube structure may be configured in any other suitable form, such as in a stethoscope type configuration.

In these embodiments, the PPG sensor 205 measures pulmonary capillary blood flow. In some embodiments, the PPG sensor 205 generates infrared (IR) light to measure the pulmonary capillary blood flow. In these embodiments, the PPG sensor 205 is a non-invasive, inexpensive, and convenient diagnostic tool to measure oxygen saturation, blood pressure, and cardiac output. In many embodiments, the PPG sensor 205 is placed at the top right of the casing 102 and may be connected to one or more additional microcontrollers.

Embodiments also include an Inertial Measurement Unit (IMU) sensor 206 for capturing seismic and auscultation signals that are indicative of the pulmonary health of the user. The IMU sensor 206 includes an IMU sensor signal enhancing material 116 that amplifies seismic and auscultation signals. Examples of the IMU sensor signal enhancing material include, but are not limited to, sound absorbers made from porous materials, micro-perforated plates, and micro-perforated panel absorbers backed with mechanical impedance plates where the backed cavity is limited as well as combinations thereof. The microcontroller transmits pulmonary health data received from the plurality of electrodes 104, 106, and 108, the microphonic sensor 202, the PPG sensor 205, and the IMU sensor 206 to the HED and a computing device such as the server 306 illustrated in FIG. 3.

In many embodiments, the casing 102 includes a lens 114 configured to envelop the camera of the HED 112. The lens 114 may be configured to cover all or a portion of the camera of the HED 112. In some of these embodiments, the lens is configured to block all or a portion of the external light when the HED 112 shines light into the skin of the patient and simultaneously captures images or records video of the skin. In some embodiments, video in additional to or instead of one or more images may be recorded by the camera.

The camera is used to record one or more images of the user's skin and the one or more images are analysed by the system using machine learning to aid in providing insights into the pulmonary health of the user based on differences in the user's tissue color detected and applying machine learning such as applying one or more image recognition machine learning models with the one or more images to aid in providing insights into lung conditions.

In several embodiments, the casing 102 includes a battery configured to supply electrical power to the circuit board 110. In some instances, the battery may receive power from an external source. The casing 102 may connect with the HED 112 through a power cable 206 or any other suitable connection. In several embodiments, the casing 102 includes one or more additional sensors such as seismic and microphonic sensors which can used to facilitate the identification of common ambient environmental noise unrelated to the patient's pulmonary health. In some embodiments, the presence of data indicating a high severity of a lung disease triggers the transmission of one or more messages to a healthcare professional or other health monitor.

In many of the embodiments, the user is guided by the HED 112 through instruction, for example visual or audio instruction, as to where to place the device on the user's body. In some embodiments, the instructions may indicate corrective actions the user can take to optimally place the HED 112 on a user. Additionally, in many embodiments, previously collected sensor data is used to identify a user's unique physiological markers.

Figure 3:
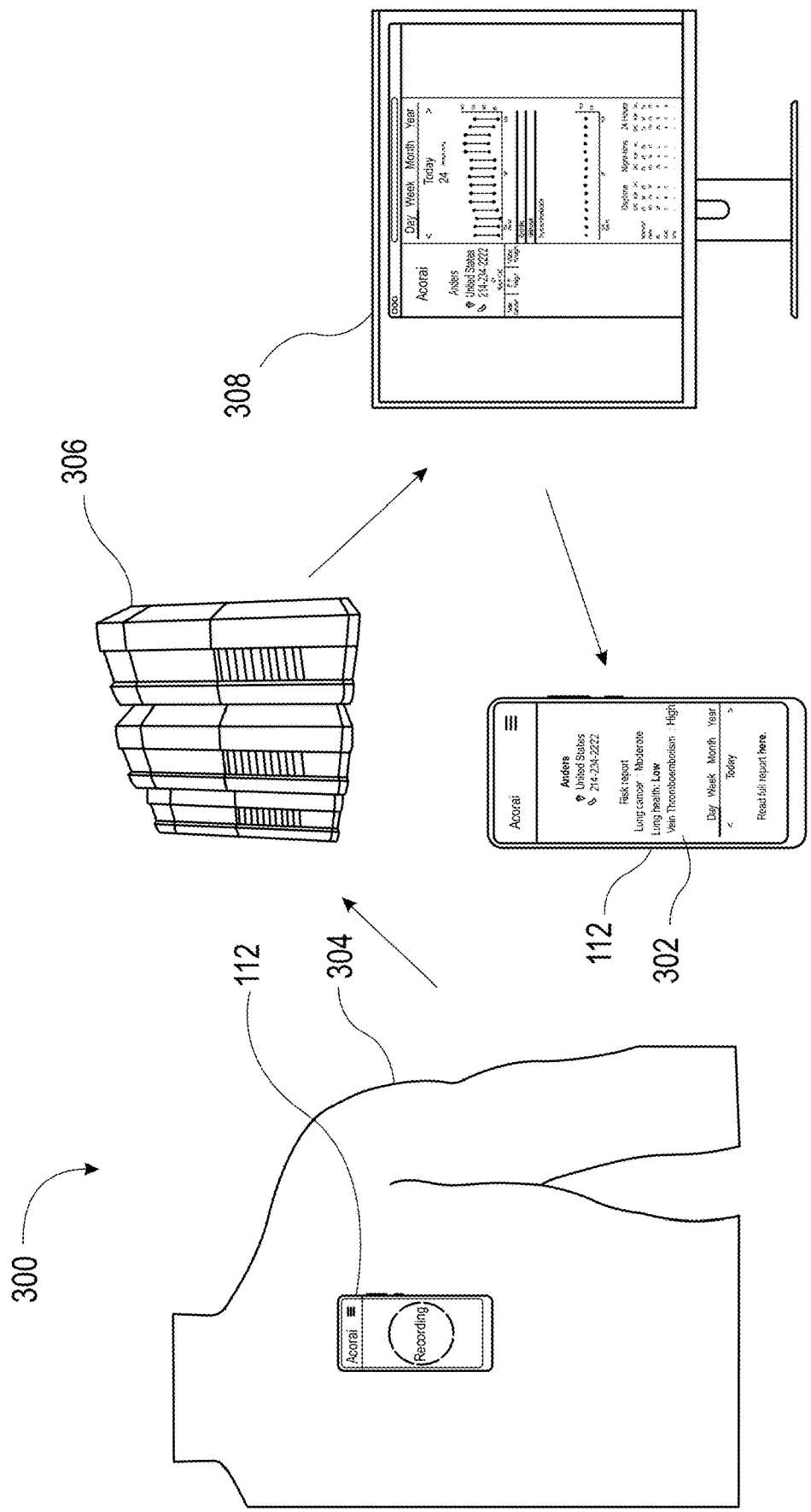
FIG. 3 illustrates a network implementation of the pulmonary health assessment system in accordance with embodiments of the claimed subject matter.

FIG. 3 illustrates a network implementation of the present pulmonary health assessment system 300, in accordance embodiments of the claimed subject matter. In several embodiments, the HED 112 includes a display screen 302 for displaying pulmonary diagnostic information using pulmonary health data received from the microcontroller. In many embodiments, the casing 102 is configured with the HED 112 is positioned against the chest of the user 304 so it can capture the user's pulmonary health data. In other embodiments, the casing 102 is configured to capture the user's pulmonary health data when the HED 112 is positioned against the back of the user.

In some embodiments, the HED 112 is positioned and secured within the casing 102. The HED 112 includes a processor to execute a plurality of instructions according to the requirements of one or more pulmonary monitoring applications. In many embodiments, the processor is configured to display one or more commands, for example audio or visual commands, so that the user or a third party can position the casing 102 against the chest of the user. Similarly, the processor can also instruct a user or a third party to position the HED 112 to optimize the sensor data acquisition. In many embodiments, the processor commands include an instruction to the user or a third party operating the HED 112 to position and hold the casing 102 against the user in a particular manner such as holding it against the user with one hand.

In many embodiments, the classification model is trained to detect an unhealthy lung, for example a user's lung affected by severe acute respiratory syndrome (SARS). The classification model is trained based on data received from one or more of computerized tomography (CT) scans of the lung, X-ray of the chest, and spirometer data, magnetic resonance imaging (MRI) data, and ultrasound data. In some embodiments, the spirometer data is collected by a spirometer. The spirometer measures the volume of air inspired and expired by the lungs as well as ventilation, the movement of air into and out of the lungs. According to several embodiments, the computing device 306 is configured to receive, in one or more temporal windows, a representation of one or more of the following: the IMU sensor, the plurality of electrodes, the PPG sensor, and the microphonic sensor signal recorded by the casing 112.

In these embodiments, the computing device 306 is configured to detect features of the IMU sensor, the PPG sensor, and the microphonic sensor from at least one or more portions of the received representations falling within each of the one or more temporal windows.

The computing device 306 is additionally configured to identify patterns of the features of respective sensors from within the one or more portions based on at least one of the following: a classification model and a regression model.

The computing device 306 is configured to calculate, based on the identified patterns, a probability of whether one or more portions correspond to a problem with the pulmonary health of the user. In many embodiments, the classification model is trained to detect an unhealthy lung due to lung cancer.

In many embodiments, the processor is configured to transmit the data indicative of pulmonary health from the handheld electronic device 112 to a server 306 over a network; and store the data in the server 306 for subsequent analysis by a clinician. Examples of the network could be one or more networks, or a combination of a local area network and a wide area network, such as the internet, using any suitable physical or a wireless connections, for example, Wifi, Ethernet and Bluetooth connections. One or more wireless networks may any network known to those skilled in the art, including by not limited to, a GSM, 3G, 4G, and a 5G network. In some embodiments, the processor is configured to transmit the data indicative of pulmonary function from the HED 112 to a clinician computing device 308 via the internet for use with remote diagnostic analysis and processes such as machine learning.

In many embodiments, the clinician computing device 308 performs risk analysis which can be presented in any desired visual and/or audio formats using the mobile application of the HED 112. Also in many of the embodiments, the classification model is trained to detect abnormal lung activity. In several embodiments, the microcontroller utilizes a de-noising algorithm, for example TensorFlow Lite which includes a machine learning library.

Figure 4:
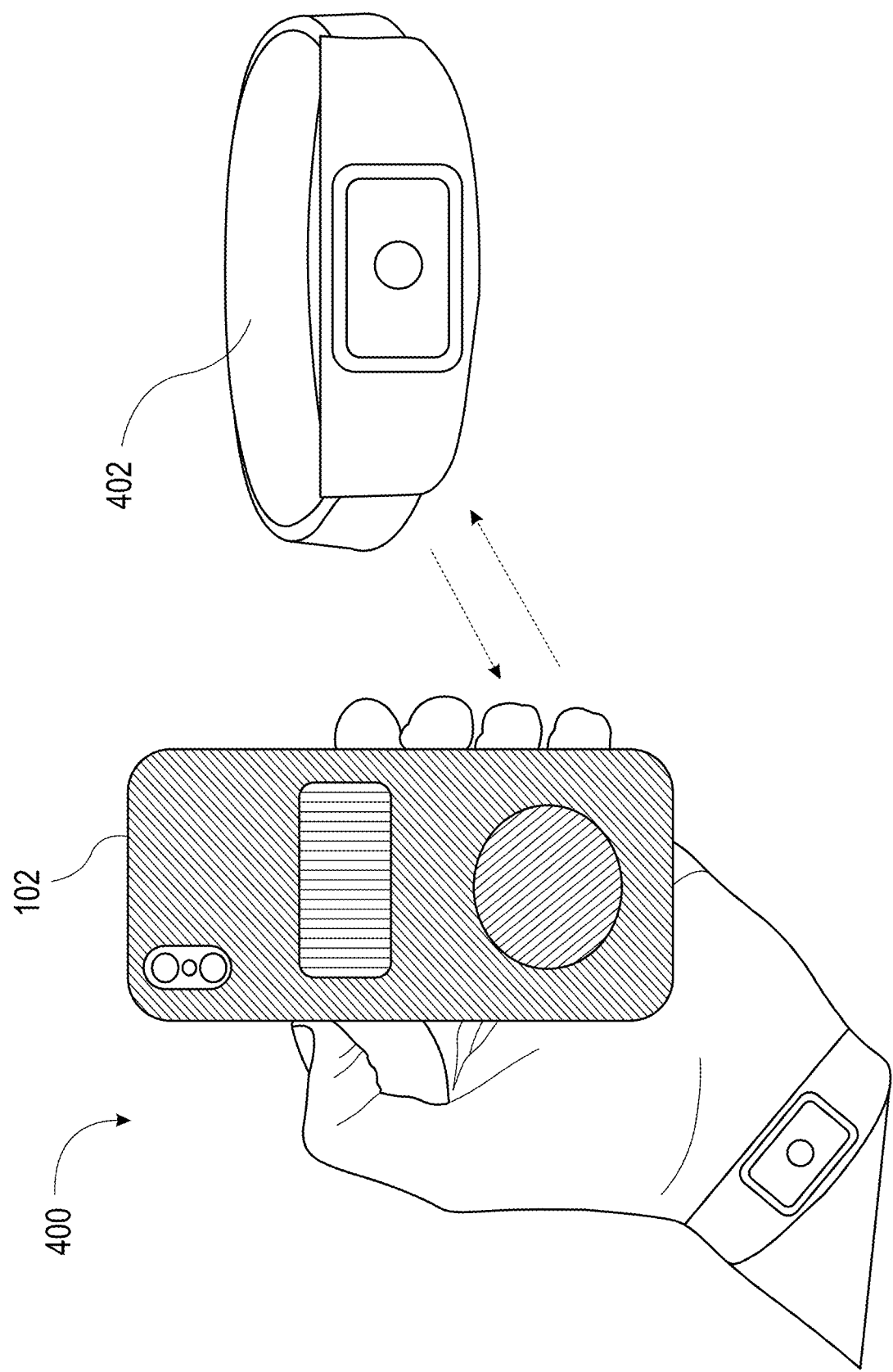
FIG. 4 illustrates a perspective view of communication between the casing and a second handheld electronic device in accordance with embodiments of the claimed subject matter.
Figure 5:
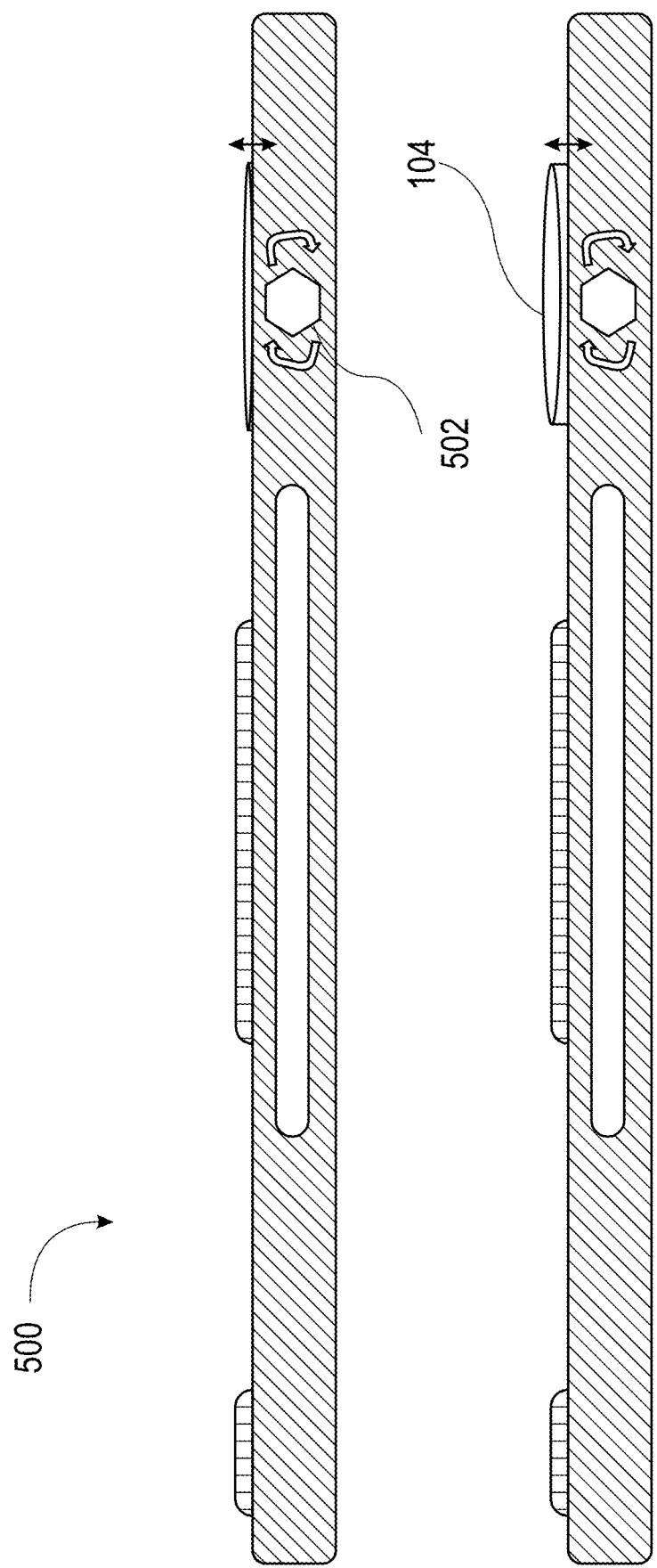
FIG. 5 illustrates a side view of the casing in accordance with embodiments of the claimed subject matter.

FIG. 4 illustrates a perspective view of a system 400 having communication between the casing 102 and a second handheld electronic device 402, in accordance with several embodiments. In some embodiments, the pulmonary health assessment system includes a second handheld electronic device 402 that includes a HED wireless transceiver and an application. The HED wireless transceiver receives pulmonary health data from the casing 102 and establishes a communication with the server for transmission of pulmonary health data there-between. The HED based application is programmable to transmit diagnostic information derived from the pulmonary health data received by the HED wireless transceiver. In some embodiments, the second handheld electronic device 402 is a wearable device which can connect wirelessly with the handheld electronic device 112. Examples of the second handheld electronic device 402 include "smartphones", "smartwatches," PCs, tablets, or handheld computers which can download and examine data in real-time and/or in a different temporal segment. FIG. 5 illustrates a side view 500 of the casing 102 in accordance with embodiments of the claimed subject matter. The casing 102 includes a button 502 which can be used to initiate the operation (in/out) of the first ECG electrode 104 so that electrical signals may be captured by the electrode 104.

Many embodiments include various sensors employing different technologies allowing for robustness across different recording environments and patients. For instance, in a noisy environment the classification model and/or regression model may be trained to emphasize visual or seismic sensors. In another example wherein the embodiment is used with a darker skinned patient wherein light is less able to penetrate the skin adequately, the classification model and/or regression model may be trained to emphasize sensors pertaining to audio and/or electrophysiological sensors.

In other embodiments, the classification model is trained to detect the presence of an deficiency in a lung caused by a pulmonary embolism. In some of the embodiments, the processor is configured to provide instructions pertaining to the management of the user's disease. Also, in many of the embodiments, the casing 102 includes an ultrasound transducer, a magnet, radiofrequency coils, and a gradient coil. In many embodiments, the casing 102 is configured to capture pulmonary health data of the user when positioned against the thoracic cavity of the user.

According to some embodiments, a physiological identification system includes a pulmonary health assessment device that utilizes a plurality of sensors and a computing device. In these embodiments, the computing device is configured to determine the identity of a user based on a plurality of unique physiological features of a user based on data from the pulmonary health assessment device's previous measurements. In many of these embodiments, the plurality of sensors include one or more of the following: a microphonic sensor, a Photoplethysmography (PPG) sensor, an Inertial Measurement Unit (IMU) sensor, and an ultrasound transducer.

According to many embodiments of the health assessment device placement calibration system, a pulmonary health assessment device is equipped with a plurality of sensors and a display (screen) configured with one or more computing devices to display a plurality of instructions. Other embodiments may include a speaker in addition to a screen to broadcast audio instructions in addition to or instead of visual instructions. In some embodiments, the pulmonary assessment device is configured to perform the steps of: determine the placement of said health assessment device based on unique physiological features of a user pertaining to one or more previous measurements from the pulmonary health assessment device, and provide instructions of placement of the health assessment device through the display screen and/or the audio speaker. Other embodiments may include a touch instruction such as with the use of braille for visually impaired users. In many embodiments, the health assessment device placement calibration system includes one or more additional handheld electronic devices that transmit data to one or more computing devices to indicate the position of the health assessment device on the user's body. The one or more additional handheld electronic devices may employ a plurality of inertial measurement unit sensors to indicate location, angle and/or stationarity of the user.

Many of the embodiments allow the casing 102 to operate without a battery using direct power from an electronic device allowing for more space within the casing 102 so that larger and more powerful sensors may be used with the embodiments leading to enhanced data collection quality and accuracy. The absence of a battery may also help reduce the amount of electrical interference relating to the use of the casing's sensors. These embodiments allow for more powerful devices that alleviate the need to have multiple pulmonary health assessment devices to be able to identify a number of different lung conditions. Using a single device that can accurately analyse a number of the lung conditions instead of multiple devices, the patient experience can be substantially improved helping ease the patient's anxiety and leading to more willingness to use the device for regular monitoring.

The utilization of the HED 112 with the casing 102 allows greater accuracy and efficiency of data transmission. Data relating to external noise, positioning and movement of the HED 112 (and the attached casing 102) can be measured using the HED's internal accelerometer, microphonic and other sensors. Additional sensors may be added to increase the data input for additional external information. This measured data can be used to help remove noise from other collected health related data so that analysis can be made on data that is most relevant to conditions pertaining to pulmonary health of the user. In many embodiments, the HED 112 internal accelerometer and microphonic sensor act as an acoustic sensor that provides an acoustic signal conveying information associated with internal respiratory sounds. In these embodiments, the acoustic sensor can sense tissue vibration.

Embodiments using smartphones allow a simplified means for a user to monitor their own health. The user can carry the embodiments throughout the day and night and the casing 102 can also function as a protective barrier against breakage, surface scratching and damaging environmental hazards such as water. Another benefit of the embodiments is the use of a single device instead of multiple devices for self-health monitoring which can also reduce the likelihood of misplacing the device. The embodiments also allow the use of battery power instead of or in addition to power from being wired to outlets allowing users to charge the embodiments at their convenience such as at regular times during the day or night. Another benefit of the embodiments is the ability of a user to record at standardized time intervals.

In use, a patient may use the HED's one or more internal alarm clocks to remind the user as well as prompt the user to perform data recording functions using the embodiments. In many embodiments, the user can take readings at approximately the same time each day to allow the data collection to be performed during similar recording environments leading to a more standardized data collection to further aid in the reduction of noise in the collected data.

Figure 6A:
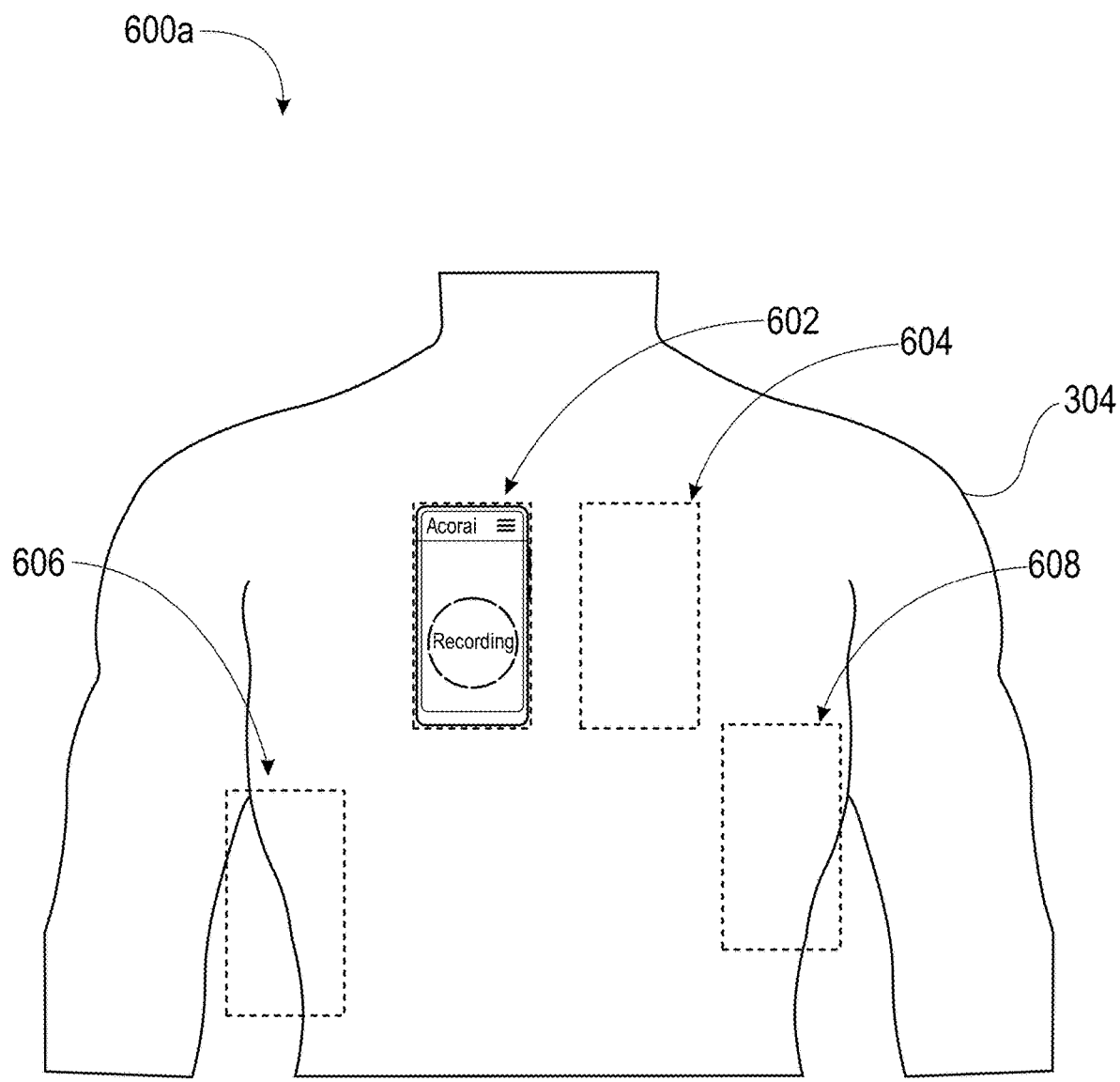
FIG. 6a illustrates a perspective view of the placement of the casing on the patient's chest and rib cage in accordance with embodiments of the claimed subject matter.

FIG. 6a illustrates a perspective view 600a of the placement of the casing 102 on the patient's chest and rib cage in accordance with at least one embodiment. FIG. 6a is explained in conjunction with FIG. 1. As shown in FIG. 6a, the casing 102 is placed centrally on the patient's chest. In many of the embodiments, the software application executed on the mobile phone (or a remote server) may be used to direct the user 304 of the casing 102 to position or correct the placement of the casing 102 on the chest of the user 304 or another person. Audio, visual or tactile instructions or directions originating from the embodiment may include a first step 602 of placing the casing 102 in a position about a finger length's distance below the patient's right collarbone, alongside the sternum, and then in a second step 604, placing the casing 102 in a position about a finger length's distance below the patient's left collarbone alongside the sternum.

Figure 6B:
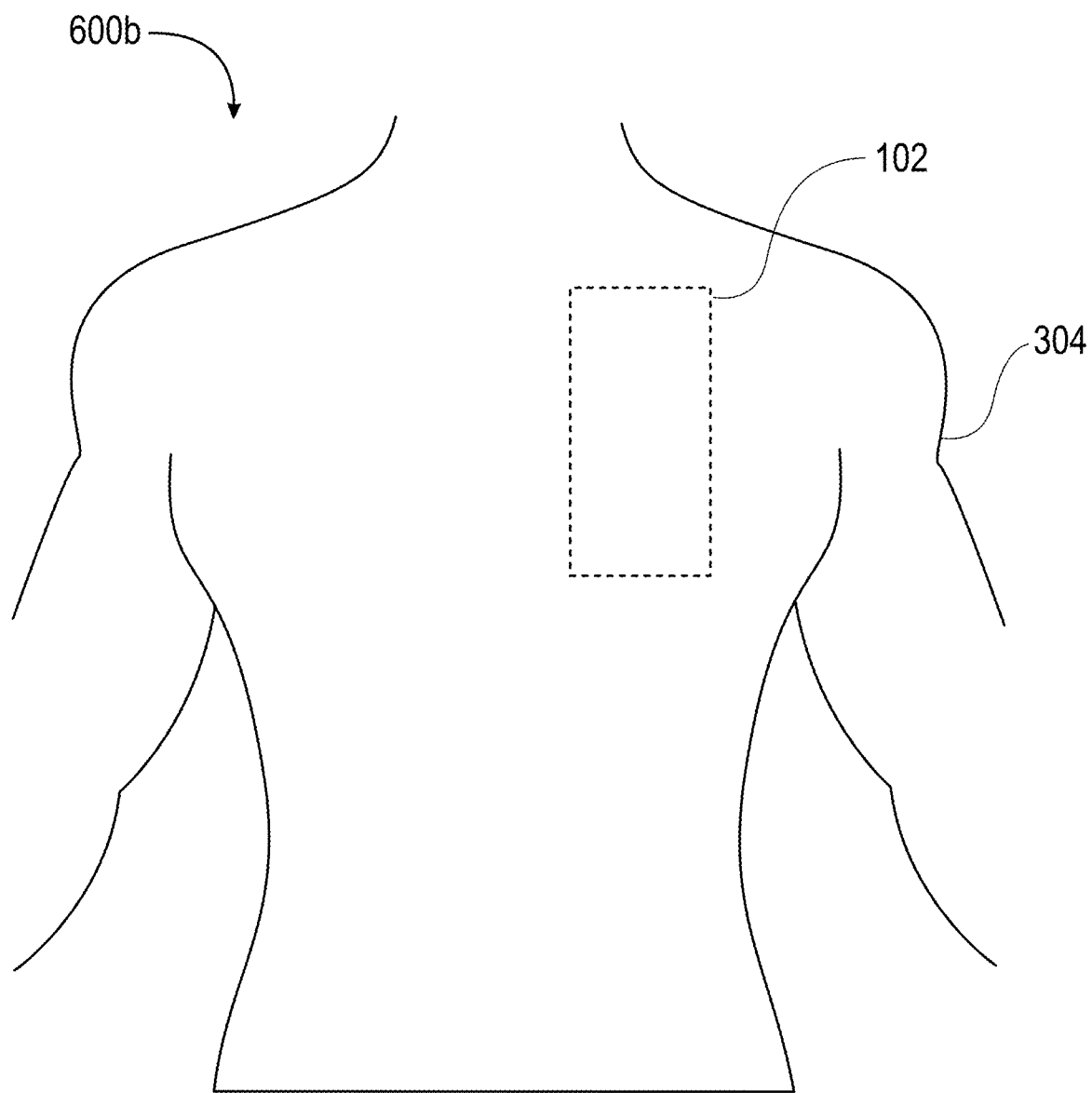
FIG. 6b illustrates a perspective view of the placement of the casing on the back portion of the patient's body in accordance with embodiments of the claimed subject matter.

Next, in a third step 606, the user is instructed to place the casing 102 on the exterior of the right rib cage of the patient and, in a fourth step 608, the user is instructed to place the casing on the outer surface at the left rib cage of the patient so that steps 602 through 608 allow the embodiments to capture the user's pulmonary health data. FIG. 6b illustrates a perspective view 600b of the placement of the casing 102 on the back portion of the user's 304 body in accordance with at least one embodiment. In this position against the back of the user 304, the embodiment can capture the pulmonary health data of the user 304.

Figure 7:
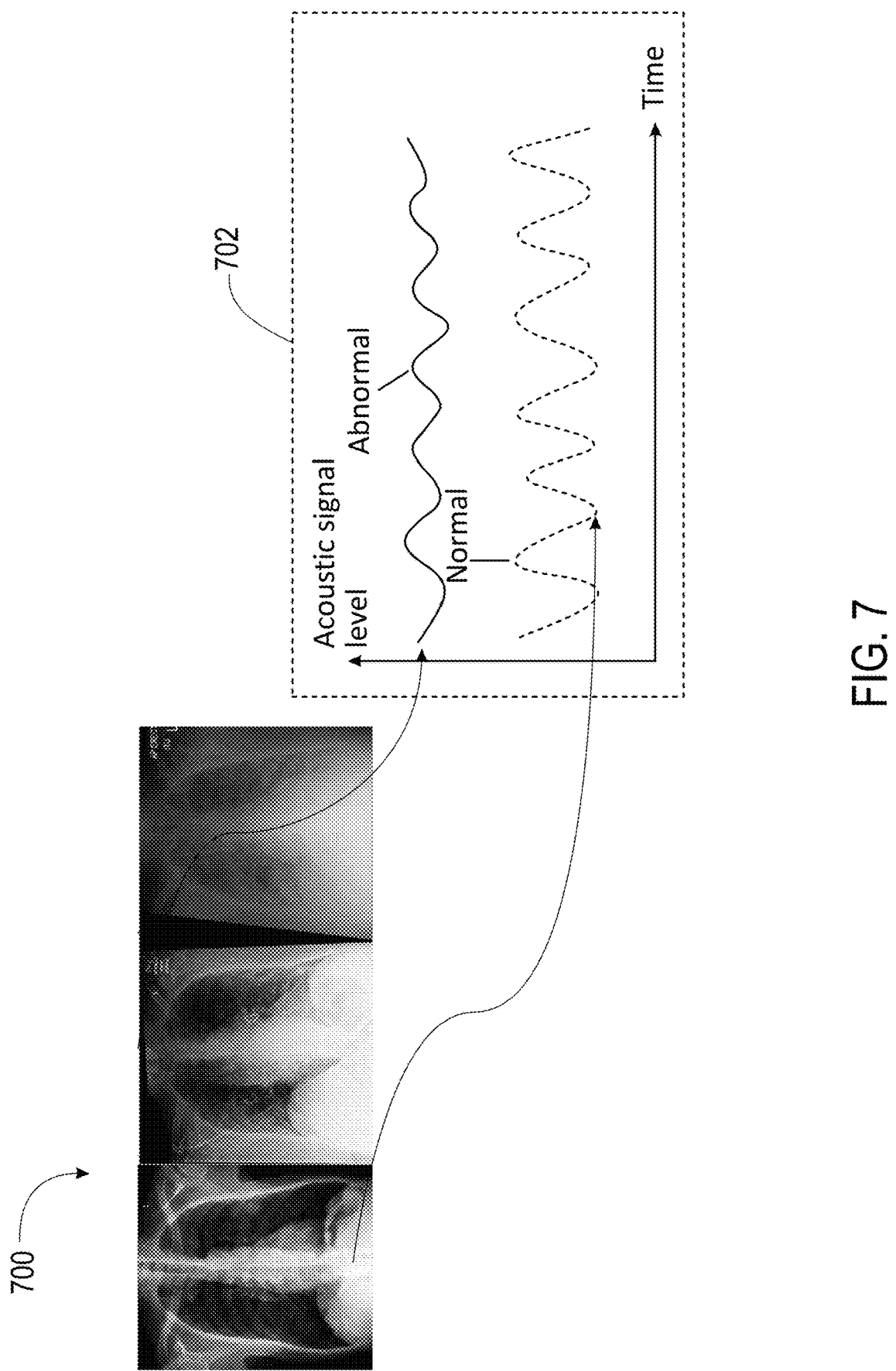
FIG. 7 illustrates a perspective view of the unhealthy lung due to Severe Acute Respiratory Syndrome (SARS) in conjunction with a graphical representation of the acoustic signal level as used in according with embodiments of the claimed subject matter.

FIG. 7 illustrates a perspective view 700 of an exemplary images of lungs including an image of an unhealthy lung affected by the Severe Acute Respiratory Syndrome (SARS) along with graphical representations 702 of acoustic signal levels in accordance with several embodiments. In these embodiments, the classification and/or regression models may be trained on data collected by the sensors using one or more of the following diagnostics: CT-scans of lungs (which is considered the "gold standard" by many practitioners), chest X-rays, Spirometers, MRIs, Ultrasounds, as well as any other suitable diagnostic system or process providing information about the lung health of a patient.

In some embodiments, image-based indications of pulmonary health, including the above described lung health information, may be used in any suitable manner to derive a clinical diagnosis probability. For example, information from an image may be used as a marker leading to a binary outcome of clinical diagnosis based on that image information. In another example, the image information may be used to calculate a percentage that could be used to represent the severity of the pulmonary health condition of the lung or lungs shown in the image. In many embodiments, the clinician's diagnoses may be used to train the models alone or in conjunction with other methods.

Figure 8C:
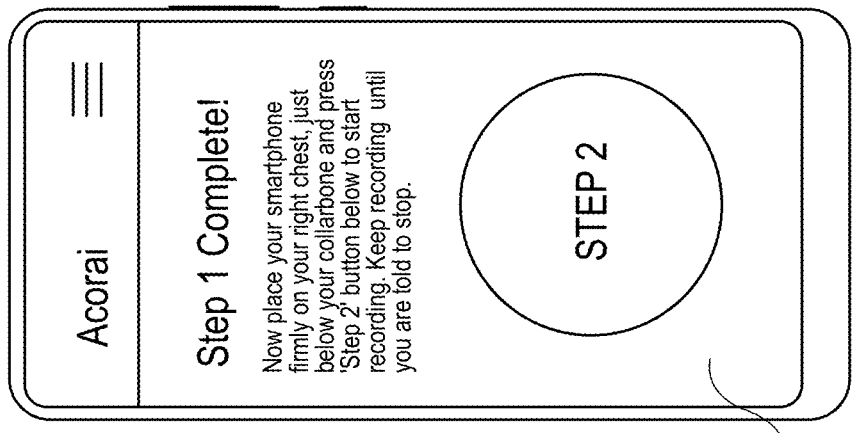
FIGS. 8a-8c illustrate a plurality of user interfaces depicting a plurality of directions pertaining to the usage of the casing in accordance with embodiments of the claimed subject matter.
Figure 8B:
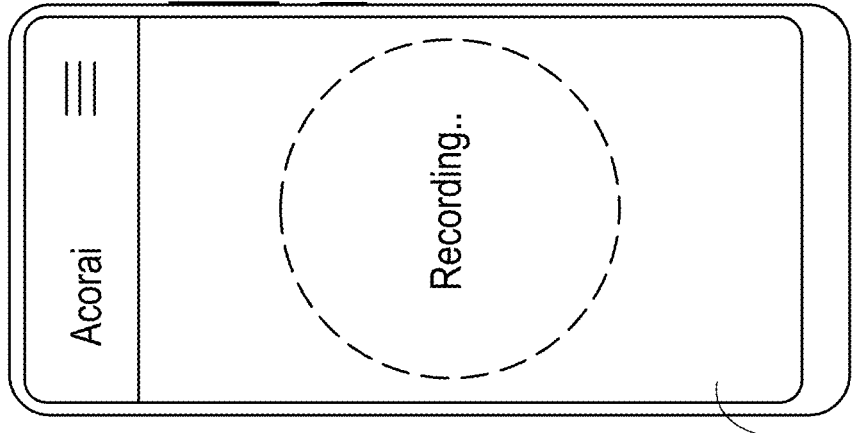
Figure 8A:
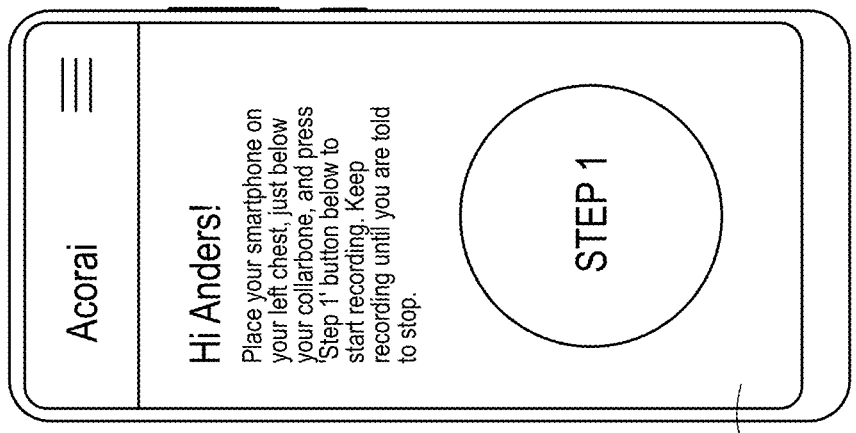

FIGS. 8a-8c illustrate a plurality of user interfaces 800a, 800b, and 800c depicting a plurality of visual directions pertaining to the usage of the casing 102 in accordance with many embodiments. The user interface 800a depicts an exemplary first step visual instructing the user to place the HED a finger below the patient's left collarbone and press the 'Step 1' button shown on the lower portion of the HED screen in order to start the recording which is shown in process in user interface 800b.

In these embodiments, the user maintains the position of the casing 102 allowing the embodiment to keep recording until the software application notifies/announces that the recording has stopped. After the recording has stopped, the user interface 800c depicts the visual text "Step 1 complete!" and further instructions for the user to first place the device firmly on his/her right chest positioned just below the collarbone and then press the 'Step 2' button below the text in order to start the recording. After the recording has stopped, the software application notifies the user that she or he can stop holding the device in the referenced recording position.

Figures 9A, 9B, 9C:
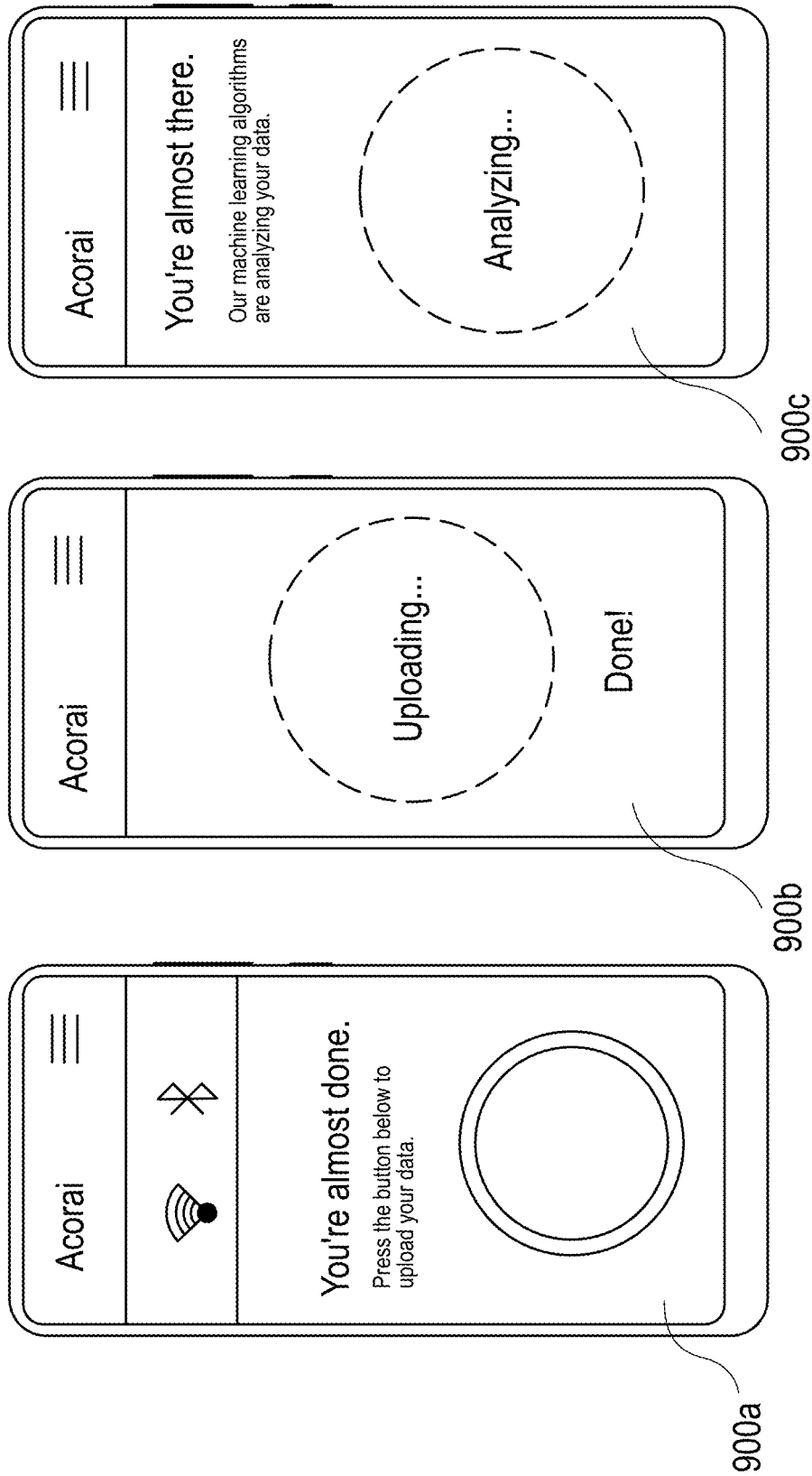
FIGS. 9a-9c illustrate a plurality of user interfaces used with operations performed by mobile applications in accordance with embodiments of the claimed subject matter.

FIGS. 9a-9c illustrate user interfaces 900a, 900b, and 900c which depict operations performed by the mobile application in according with many embodiments. The user interface 900a shows the mobile application directing the user to begin an upload of the pulmonary health data received from the plurality of electrodes, the microphonic sensor, and the IMU sensor. The user interface 900b depicts the pulmonary health data being uploaded and finishing the upload. The user interface 900c depicts the pending analysis of the pulmonary health data. The analysis performed using the pulmonary health data can aid in determining one or more preferred placements of the casing 102 on future sessions of the same user or positioning the casing 102 with other users. The analysis can also help with standardized data collection methods and techniques across a wide spectrum of issues and across a number of users.

In many of the embodiments, the mobile application stores and is able to use previously stored data relating to certain physical features and/or characteristics associated with a patient's pulmonary signals (and potentially other sensor data associated with the user) which may be interpreted as the patient's unique "pulmonary ID". This unique identifier can help ensure that the data collected can be verified as belonging to the patient and not someone else. The data may also be used to identify one of multiple users that may be sharing the same device and it may also be used to determine when a patient has placed the casing 102 in a wrong position and prompt that patient to reposition the casing 102.

In some embodiments, the data collected through the casing 102 may be combined with other data, for example data sent from a wearable electronic device. By using additional data from other sources with the initial data, such as the data sent from a wearable sensor worn on the wrist of a patient, enhanced accuracy may be achieved. For instance, the combination of data can help calculate pulse transit time and aid in the comparison of data between different parts of the body sensed at the same time. Some embodiments may used additional data from measurement readings of pulse oximetry devices as well as any other information related to pulmonary health. In many embodiments, the casing 102 may be used with a wireless charging station allowing the one or more devices to be wirelessly charged. Also in many embodiments, a battery-less wearable may be connected to the casing 102 and used for simultaneously recording data while drawing power directly or indirectly from the casing 102.

After the data is recorded, it can be analysed in the connected HED or another connected computing device or the data may be uploaded to one or more servers where it can be analysed. The data may also be analysed by any combination of computing devices and servers. Embodiments may use any suitable methods for data analysis including, but not limited to, machine learning-based methods that are used to classify whether or not certain lung conditions are indicated in the data as being present. The machine learning methods used in the embodiments include, but are not limited to, decision tree-based machine learning methods, artificial neural networks, convolutional neural networks, logistic regression, naive Bayes, nearest neighbour, support vector machines, boosted tree learning methods, and deep learning methods.

Figure 10:
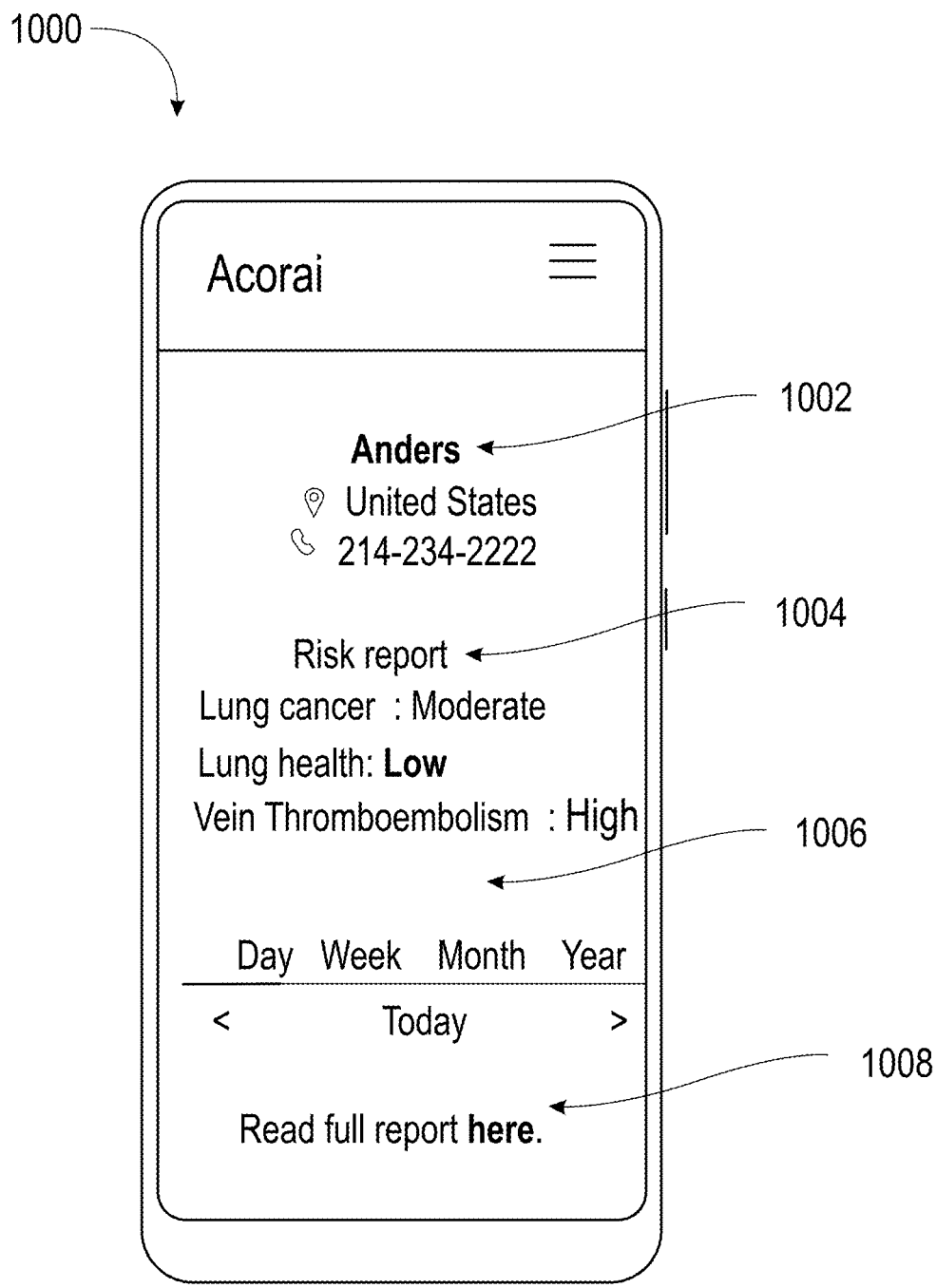
FIG. 10 illustrates a user interface used to depict personal information and pulmonary diagnostic information pertaining to the user in accordance with embodiments of the claimed subject matter.

FIG. 10 illustrates a user interface 1000 depicting personal information and pulmonary diagnostic information pertaining to a specific user in accordance with several embodiments. The results of the data analysis are presented to the patient via the mobile application and they may also be presented instead or in addition to another person of the patient's choice using any suitable methods including visually, audibly and/or tactile methods. In one example, an email can be sent to the patient's clinician with a report of the recording. Block 1002 of the user interface 1000 shows the patient name and contact information. Block 1004 of the user interface 1000 shows exemplary results from an analysis of the user's pulmonary health data. Block 1006 shows an exemplary option for the user to view and compare past recordings and block 1008 shows an exemplary option allowing a third party such as the user's physician to manually review by viewing and listening to each recording.

In some embodiments, a speaker configured to emit an audible noise may be used in conjunction with the HED. The speaker may be any suitable speaker known to those skilled in the art or it may be include more than one speaker working independently or together. The speaker may be attached to the HED or it may be used as an external speaker with the HED with any suitable communication means between the speaker and the HED such as a wired or wireless connection. In these embodiments, the speaker can be used to emit a noise that can be reflected back and analyzed with one or more sensors such as internal or external microphones used with the HED. The resulting reflected noise or noises can be used by the embodiments to provide insights into obstruction, abnormalities and pulmonary health of the user including the health of the user's lungs. In many of these embodiments, while recording using the HED as described herein, the user may be prompted by the pulmonary monitoring application to make a low, continuous and/or droning sound which may aid in that user's pulmonary health assessment.

FIG. 11 illustrates a flow diagram 1100 of using data for model training in accordance with embodiments of the claimed subject matter. Step 1102 shows the use of summary statistics of each time series data pertaining to a plurality of the patients. Step 1104 shows the use of multiple summary statistics with comparison algorithms to generate new features. Step 1106 shows the use of the new datasets to train new machine learning models and step 1108 shows the step of creation of a final predictive model based on the training of the machine learning models. Various other combinations of methods may be used to train any number of models which can be used for data analysis.

Unless otherwise defined, all terms (including technical and scientific terms) used in this disclosure have the same meaning as commonly understood by one of ordinary skill in the art to which this disclosure belongs. It is to be understood that the phrases or terms used with the present inventive subject matter is for the purpose of description and not of limitation. As will be appreciated by one of skill in the art, the present disclosure may be embodied as a device, system, and method or computer program product. Further, the embodiments may take the form of a computer program product on a computer-readable storage medium having computer-usable program code embodied in the medium. The present systems, devices and methods have been described above with reference to specific examples, however, other embodiments and examples than the above description are equally possible within the scope of the claimed subject matter. The scope of the disclosure may only be limited by the appended patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art. The scope of the embodiments of the inventive subject matter is ascertained with the claims as submitted at the time of filing the complete specification.

What is claimed is:

1. A pulmonary health assessment system for use with a handheld electronic device, the pulmonary health assessment system comprising:

a handheld electronic device (HED);
a casing having a shape adapted to secure the HED with the casing comprising:
a plurality of ECG electrodes comprising:
a rust ECG electrode placed on an outer surface of the casing; and
a second ECG electrode and a third electrode placed on each side of the casing to facilitate a thumb and fingers of a user to be placed on the casing having the shape that is adapted to secure the handheld electronic device, wherein the plurality of ECG electrodes are configured to capture data indicative of the pulmonary health of the user;
a circuit board configured within the casing and electrically connected with the plurality of ECG electrodes and at least one microcontroller, wherein the circuit board comprises:
a microphonic sensor for capturing pulmonary audio signals indicative of the pulmonary health of the user;
a Photoplethysmography (PPG) sensor for measuring pulmonary capillary blood flow indicative of the pulmonary health of the user,
an Inertial Measurement Unit (IMU) sensor for capturing seismic and auscultation signals indicative of the pulmonary health of the user, and
a diaphragm to enhance the pulmonary audio signals captured by the microphonic sensor;
wherein the at least one microcontroller is configured to transmit pulmonary health data received from the plurality of ECG electrodes, the microphonic sensor, the PPG sensor, and the IMU sensor to at least one of the HED and a computing device, wherein the computing device is configured to:
receive, in one or more temporal windows, a representation of data from one or more of the following: the IMU sensor, the plurality of ECG electrodes, the PPG sensor signals, and the microphonic sensor signals;
detect features from at least one or more portions of the received representations of data that fall within each of the one or more temporal windows;
identify patterns in the detected features based on one or more of the following models: a classification model and a regression model; and
using the identified patterns, calculate a probability of whether the identified patterns correspond to a problem with the pulmonary health of the user; and
a second handheld electronic device worn by the user, wirelessly connected with the HED, wherein the second handheld electronic device comprises:
one or more sensors to collect health data from the user; and
a HED wireless transceiver configured to establish a communication between the HED and the computing device to transmit pulmonary health data therebetween, wherein the computing device is configured to:
detect, based on the classification model, the presence of indicators of a lung disease, and
estimate using the indicators of the lung disease, based on the regression model, a severity of the lung disease.

2. The pulmonary health assessment system according to claim 1, wherein the PPG sensor further generates infrared (IR) light to indicate pulmonary health.

3. The pulmonary health assessment system according to claim 1, wherein the HED secured within the casing further comprises a display screen to display pulmonary diagnostic information derived from the pulmonary health data received from the microcontroller.

4. The pulmonary health assessment system according to claim 1, wherein the casing is configured to capture pulmonary health data of the user when the casing is positioned against the user's chest.

5. The pulmonary health assessment system according to claim 1, wherein a speaker is configured to emit noise which is reflected back, sensed by one or more sensors wherein the reflected noised is utilized to provide an assessment of the user's pulmonary health.

6. The pulmonary health assessment system according to claim 1, wherein the HED secured within the casing further comprises a processor to execute a plurality of instructions pertaining to a pulmonary monitoring application, wherein the processor is configured to communicate one or more commands to position the casing against the user's chest.

7. The pulmonary health assessment system according to claim 1, wherein the classification model is trained to detect features of an unhealthy lung caused by severe acute respiratory syndrome (SARS).

8. The pulmonary health assessment system according to claim 1, wherein the classification model is trained based on data received from one or more of the following: computerized tomography (CT) scans of the lung, X-ray of the chest, spirometer data, magnetic resonance imaging (MRI) data, and ultrasound data.

9. The pulmonary health assessment system according to claim 1, wherein the casing further comprises a heat-sensing camera for detecting chest skin surface temperature wherein variations in temperatures can be used to help assess the health of the user.

10. The pulmonary health assessment system according to claim 1, wherein the diaphragm comprises an enhancer unit for enhancing the pulmonary audio signals including the ability to amplify low-frequency auscultation signals in the pulmonary audio signals.

11. The pulmonary health assessment system according to claim 1, wherein the casing further comprises a battery configured to supply electrical power to the circuit board.

12. The pulmonary assessment system according to claim 1, wherein the casing further comprises a lens configured to envelop a camera of the HED.

13. The pulmonary health assessment system according to claim 1, wherein the casing further comprises the lens configured to block external light when the HED shines a light onto the skin of the user;
wherein the light is used to help with the recording of one or more images of the skin of the user, and
wherein the one or more images are analysed based on machine learning in order to provide insights into the pulmonary health of the user.

14. The pulmonary health risk assessment system according to claim 1, wherein the casing further comprises one or more seismic and microphonic sensors to facilitate identification of common ambient environmental noise unrelated to the patient's pulmonary health.

15. The pulmonary health risk assessment system according to claim 1, wherein data indicating a high severity of a lung disease triggers a message transmission to a healthcare professional.

16. The pulmonary health risk assessment system according to claim 1,
wherein the user is guided through instruction from the HED as to where to place the device on the user's body.

17. The pulmonary health risk assessment system according to claim 1, wherein the system identifies unique physiological markers of the user comprising previously collected sensor data.

18. The pulmonary health assessment system according to claim 1, wherein the classification model is trained to detect features of an unhealthy lung caused by lung cancer.

19. The pulmonary health risk assessment system according to claim 1, wherein the processor is configured to provide instructions to the user regarding the management of the user's disease.

20. The pulmonary health assessment system according to claim 1, wherein the casing further comprises an ultrasound transducer.

21. The pulmonary health assessment system according to claim 1, wherein the casing further comprises one or more of the following: a magnet, radiofrequency coils, and a gradient coil.

22. The pulmonary health assessment system according to claim 1, wherein the casing is configured to capture pulmonary health data of the user when positioned against the thoracic cavity of the user.

\* \* \* \* \*